(12) United States Patent
Becvar et al.

(10) Patent No.: US 6,673,563 B1
(45) Date of Patent: *Jan. 6, 2004

(54) LUMINOUS BACTERIA AND METHODS FOR THE ISOLATION, IDENTIFICATION AND QUANTITATION OF TOXICANTS

(76) Inventors: James E. Becvar, 5444 La Estancia, El Paso, TX (US) 79901; Laura E. Becvar, 5444 La Estancia, El Paso, TX (US) 79901

( * ) Notice: Subject to any disclaimer, the term of this patent is extended or adjusted under 35 U.S.C. 154(b) by 0 days.

This patent is subject to a terminal disclaimer.

(21) Appl. No.: 09/954,841

(22) Filed: Sep. 18, 2001

Related U.S. Application Data

(63) Continuation of application No. 09/390,525, filed on Sep. 3, 1999, now Pat. No. 6,340,572, which is a continuation of application No. 07/680,678, filed on Apr. 4, 1991, now Pat. No. 6,017,722.

(51) Int. Cl.$^7$ ............................ C12Q 1/66; C12Q 1/18; G01N 35/554

(52) U.S. Cl. ............................ 435/8; 435/7.32; 435/32

(58) Field of Search ............................ 435/7.32, 8, 32

(56) References Cited

U.S. PATENT DOCUMENTS 6,017,722 A * 1/2000 Becvar et al.

FOREIGN PATENT DOCUMENTS

| DE | WO DE 3833628 | 3/1990 |
| DE | WO 88DE626 | 10/1990 |
| EP | 153366 | 8/1984 |
| WO | WP I 88-308491 | 4/1988 |
| WO | WO 89/08500 | 3/1989 |

OTHER PUBLICATIONS

"1992 Naval National Science Award Winners," *Department of the Navy* 2 (Jun. 1992).
"El Pasoan is top winner at science fair," *El Paso Times* 1 (May 16, 1992).
"Lincoln Junior High School Science Fair," *Westside Annual* 16 (Mar. 1, 1990).
McGill, D., "Caution: Young minds at work: Regional science fair is Saturday," *El Paso Times* 3B (Apr. 23, 1993).
Ugarova et al. (1987), *Appl. Biochem. Biotechnical.*, 15 (1): 35–51.
Stom et al. (1986), *ACTA Hydrochim Hydrobiol.*, 14 (3):283–292.
Vasseur et al. (1983), Presented at the International.
Gu, Zonglian (1987), *Turangxue Jinzhan*, 15(3): 48–51.
Gu, Z. (1983), *Huanjing Kexue*, 4(5):30–3.
Bielecki (1985), *Acta Agro bot* 35(1):123–132.
Aoyama, T. (1985), *Health Phys.*, 48(6):773–80.
Liebowitz (1984), *Anal. Biochem.*, 137(1):161–63.
J. W. Hastings (1978) In: *Bioluminescence and Chemiluminescence, Methods in Enzymology*, Marlene A. DeLuca, Editor, Academic Press, vol. 57:125–135.
Hastings et al. (1978) In: *All Luminescence and Chemiluminescence Methods in Enzymology*, Marlene A. DeLuca, Editor, Academic Press, vol. 57:135–152.
Pannell et al. (1990) *Organometallics*, 9(9):2454–2462.
Merck Index, 11th ed. (1989), p. 878–879.
James E. Becvar, In: *Bioluminescence and Chemiluminescence: Basic Chemistry and Analytical Applications*, Marlene A. DeLuca and William D. McElroy, eds., Academic Press (1981), p. 583–589.
Kenneth Nealson (1978) In: *Bioluminescence and Chemiluminescence, Methods in Enzymology*, Marlene A. DeLuca, eds., Academic Press, vol. 57.
Aoyama, T., *Health Phys.*, 48(6):773–780, 1985.
Becvar, In: *Bioluminescence and Chemiluminescence: Basic Chemistry and Analytical Applications*, DeLuca and McElroy (Eds.), Academic Press, 583–589, 1981.
Bielecki, *Acta Agro bot*, 35(1):123–132, 1985.
Gu, Z., *Huanjing Kexue*, 4(5):30–33, 1983.
Gu, Zonglian, *Turangxue Jinzhan*, 15(3):48–51, 1987.
Hastings et al., In: *All Luminescence and Chemiluminescence Methods in Enzymology*, DeLuca (ed.), Academic Press, 57:135–152, 1978.
J.W. Hastings, In: *Bioluminescence and Chemiluminescence, Methods in Enzymology*, DeLuca (Ed.), Academic Press, 57:125–135, 1978.

(List continued on next page.)

*Primary Examiner*—Christopher R. Tate
*Assistant Examiner*—Michele C. Flood
(74) *Attorney, Agent, or Firm*—Stephen A. Slusher; Melody E. Clark; Steven L. Highlander

(57) ABSTRACT

Methods for the isolation and identification of a toxicant in a sample are disclosed. Luminescent biological agents (i.e., bacteria) having sensitivity to a toxicant or an isolatable component in a sample are used to provide visually discernable zones of luminescent inhibition in the presence of a toxicant (or) in the presence of an isolatable sample component as separated by paper or thin layer chromatography. Kits for use in conjunction with the identification of a toxicant in a sample are also described, which include a luminescent biological reagent as the visualizing agent. Particular examples of luminescent bacterial agents useful in the practice of the present invention include *Photobacterium leoganthi*, *Photobacterium phosphoreum*, *Vibrio fischeri*, *Vibrio harveyi* a luminescent fungi, a luminescent fish extract, a luminescent dinoflagellate and fluorescent microorganisms, such as Cypridina. Potential toxicants, in a liquid sample, a solid sample, or in a gaseous sample may be identified and further chemically characterized using the described methods. The isolation of potential toxicants in a sample through the processing of a sample through a separation phase matrix such as chromatography paper or TLC plate, followed by exposure to luminescent biological agent, provides for a rapid and inexpensive method for identifying pesticides, herbicides and heavy metals in a known or unknown sample.

22 Claims, 6 Drawing Sheets

OTHER PUBLICATIONS

Liebowitz, *Anal. Biochem.*, 137(1):161–163, 1984.
Merck Index, 11$^{th}$ ed., 878–879, 1989.
Nealson, In: *Bioluminescence and Chemiluminescence, Methods in Enzymology*, DeLuca (Ed.), Academic Press, 57, 1978.
Pannell et al., *Organometallics*, 9(9):2454–2462, 1990.
Stom et al., *ACTA Hydrochim. Hydrobiol.*, 14(3):283–292, 1986.
Ugarova et al., *Appl. Biochem. Biotechnical.*, 15(1):35–51, 1987.
Vasseur et al., (1983), Presented at the International.

* cited by examiner

Diazanon Lindane

Diazanon Lindane 5A  5B

D/  D/128  D/256  D/512  D/1024

*Diazanon Lindane*

LUMINOUS BACTERIA AND METHODS FOR THE ISOLATION, IDENTIFICATION AND QUANTITATION OF TOXICANTS

The present application is a continuation of U.S. application Ser. No. 09/390,525, filed Sep. 3,1999, now issued as U.S. Pat. No. 6,340,572, which is a continuation of U.S. application Ser. No. 07/680,678, filed Apr. 4, 1991, now issued as U.S. Pat. No. 6,017,722.

BACKGROUND OF THE INVENTION

I. Field of the Invention

The present invention relates generally to the field of methods for identifying toxicants and/or isolated component substances in a sample. The types of samples which may be analyzed include either a solid sample, a liquid sample or a gaseous sample. The present invention also relates to the field of biological toxicant identification agents, as a particularly described luminescent biological reagent, for example the luminescent bacteria, are employed in the claimed isolation, identification and quantitation methods and techniques disclosed herein. The present invention also relates to the field of toxicant detecting kits, as a kit for the identification of toxicants is described employing a luminescent biological reagent.

II. Description of the Related Art

When grown in appropriate liquid culture or on semi-solid culture media, suspensions of luminescent bacteria emit a constant level of light for extended periods. Luminescent bacteria are bacteria which emit light without excitation, (i.e., they glow in the dark). The origin of the emission is biochemical, and organisms which demonstrate this characteristic are described as exhibiting the phenomenon of bioluminescence. Most known examples of luminescent bacteria are marine. Two major subclasses of the luminescent organisms are 1) free living (*Vibrio harveyi*) and 2) symbiotic (*Vibrio fischeri, Photobacterium phosphoreum, Photobacterium leiognathi*). Other major bioluminescent organisms include fire flies (*Photinus pyralis*), crustaceans (*Cyridina hilgendorfi*), dinoflagellates (*Gonyaulax polyhedra, Notiluca militaris*), fungi (*Omphalia flavida*) and the sea pansy (*Renilla reniformis*).

The luminescence of bacteria has long been known to be sensitive to a wide variety of toxic substances (e.g., heavy metals, pesticides, etc.). The exquisite sensitivity of luminescent bacteria to a variety of substances has made them a popular choice in methods for the gross detection of the presence of toxic materials. For example, the use of luminescent bacteria has been discussed for the detection of toxins on solid surfaces, such as soil[5], and in liquid substances, such as in the analysis of waste water[3], as well an in the detection of toxins in gaseous samples[6].

Luminescent bacteria have also been employed in the detection of toxicants in marine environments.[2] For example, Vasseur et al. describe a Microtox luminescent bacterial assay for the detection of toxicants in water (*Photobacterium phosphoreum*)[2].

Another variety of luminescent bacteria used in the analysis of industrial waste water is described in the Baher patent.[3] Specifically, the *Klebsiella planticola* bacteria has been used to detect the presence of substances toxic to particular microorganisms (used to purify industrial chemical plant waste waters) indicated through monitoring the luminescence of the Klebsiella.

Luminescent bacteria have also been used for detecting the presence of specific substances in a sample, including antibiotics, heavy metals, enzyme inhibitors, pesticides, microbial toxins, volatile hydrocarbons, disinfectants, and preservatives.[6] For example, the Siemens patent describes the use of a luciferase-gene-transformed microorganism for detecting the presence of a toxicant in a sample through a demonstrated reduction in the luminescent signal emitted by the luminescent bacteria in the presence of a toxic substance[6].

Others have reported the ability to detect the presence of particular classes of chemical toxicants using luminescent bacteria, particularly phenolic compounds.[7] For example, in Strom et al., the relative toxicity of a variety of particularly defined phenolic compounds, including hydroquinone, is described using a luminescent bacterium[7].

Thus, some species and components of luminescent bacteria have been adapted for use to simply detect the general presence of a toxic substance in a sample. In the presence of toxicants, detection of the toxins is provided by an observed diminution in luminescent emission and intensity in a variety of luminescent bacteria. However, the value of the "detection" techniques currently available is limited by an inability to identify, in an isolatable form, the substance which constitutes the "detected" toxicant or foreign substance.

No methods have been described wherein a generically "detected" toxicant may be identified in an isolatable form using a luminescent bacteria. The ability to actually identify an isolated substance as a potential "toxicant" in a sample would provide a powerful industrial and-research tool. Moreover, the ability to distinguish, by positive chemical analysis, the chemical structure of an isolated toxicant (using various chemical separation techniques known to those of skill in the art) would find great potential application in research, diagnostic medicine and industrial manufacturing processes.

Standard chemical visualization techniques for the localization of separated substances employ a variety of stains and staining procedures known to those skilled in the art (i.e., coomassie brilliant blue for gel electro-phoresis of proteins; 2-Naphthol or Resoranol for paper chromatography of sugars inhydrin for amino acid analysis with TLC). However, these techniques do not identify the potential toxicity of any visualized substance in the sample. No system has been proposed wherein a reagent may be used to provide a system wherein the potential toxicity of isolated substance in a sample may also be visualized and thereby identified.

Such a novel method for the simple, inexpensive and sensitive identification of a substance(s) in a sample or product which may be potentially lethal to an organism would also facilitate the further chemical elucidation of the chemical identity of the proposed toxicant through the subsequent use of various well known chemical analysis strategies available to those of skill in the art (such as mass spectrometry, nuclear resonance spectroscopy, infrared spectroscopy, x-ray crystallography, and chromatographic analysis). Thus, the complete chemical structure and identity of the potential toxicant could be determined if such a method, capable of identifying in an isolatable form the potential toxicant, were available. Such a system would be particularly valuable in the development of strategies to remove such identified toxicants from products intended for consumer use, and also in the development of procedures to render chemically identified toxicant(s) innocuous to animals and humans.

SUMMARY OF THE INVENTION

The present invention provides a rapid and accurate method for identifying a component substance (such as a toxin/toxicants) in a sample through the use of a luminescent biological agent employed together with chromatographic resolution techniques.

While any of a variety of luminescent bacteria may be used, those species found to be most particularly preferred for use in the practice of the present invention include *Photobacterium phosphoreum, Vibrio fischeri, Vibrio harveyi* and *Photobacterium leiognathi*. However, it is to be understood that the present inventive methods, reagents and kits may be practiced using any luminescent organism whose luminescence is specifically inhibited by an isolated component substance (for example, a potential toxicant) in a sample.

The present methods, reagents and kits may be used to isolate and identify a single toxicant, a number of individual toxicants, or a group of toxicants in or on a sample in the solid, liquid, or gaseous phase.

In part, the point of novelty of the present invention resides in the ability to identifiably isolate a component substance (for example, a toxicant) contained in a sample rapidly, and without the necessity of a separate biosensitivity assay of test sample. This is accomplished, for example, by applying a potentially toxicant-containing sample to a separation phase matrix, such as a chromatography paper sheet or a thin layer chromatography plate. The sample-exposed sheet is then exposed to a luminescent biological agent (i.e., the luminescent bacteria) according to the claimed method to accomplish, in one step, both the isolation of each distinct component substance of the sample and the potential toxicity of each of the distinct components in the test sample.

For example, according to the claimed invention, an unknown sample (for example a liquid unknown sample or a concentrated extract of a larger sample which potentially contains toxicants) may be spotted or streaked near one edge of a chromatography paper sheet at several points.

Most preferably, the sample "spots" or "streaks" are air dried to eliminate the carrier solvent in which the sample was dissolved. More applications of sample(s) can be overlaid onto the respective sample spots, if necessary, and dried. The end of the chromatography sheet closest to the spotted sample edge is then placed in contact with the solvent system of choice.

In the usual situation, the solvent of the solvent system will migrate through the "spotted" sample and through the length of the chromatography paper via capillary action and along the length of the chromatography sheet, thus separating the sample into its component parts onto particular locations or "segments" on the separation phase matrix (i.e., chromatography paper).

These locations or "segments" of the separation phase matrix (which provide the isolated components of the sample) are then exposed to a luminescent biological agent, and provide for the visualiation and identification of a distinct zone of luminescent inhibition" at locations or "segments" where luminescent inhibitory components of the sample are located.

Alternatively (to the above paper chromatography method), an unknown sample could be separated using TLC by spotting the sample on a thin layer chromatography plate. Thus, the sample would be spotted, and air dried analogously to that procedure followed for paper chromatography. However, the solvent in a TLC chamber is at the bottom of the chamber and therefore the solvent migration will be upward through the TLC plate separation phase matrix.

Depending on a variety of factors, including molecular polarity, the isolatable components in the sample will resolve, on the separation phase matrix, being more soluble in the solvent than having affinity for the silica gel or other separation phase matrix.

Resolution of the components in the mixture will depend on the polarity of the molecules in the sample verses the polarities of the stationary (e.g. paper, silica or alumina) and mobile (solvent) phases. The end result in the one dimensional TLC described is a linear array of components at different locations along the length of the chromatogram. The component substances of the sample thus migrate to isolatable locations or "segments" on the plate.

Vertical sections along one side or portion of the TLC plate may be sprayed with the luminescent biological agent to visualize toxicant location. Corresponding unsprayed zones of the plate may then be scraped off and eluted with an appropriate solvent or solvent mixture. In this manner, individual toxicants may be obtained for further separation, chemical identification, or quantitation using those laboratory techniques well known to those of skill in the art.

More toxicant may be obtained for specific chemical analysis of the thus "identified" locations or segments (areas of luminescent inhibition on the chromatogram) of the separation phase matrix by eluting identical segments from a second run selected separation phase matrix (TLC or chromatography paper) that has not been exposed to the luminescent biological agent. The chemical structural identity of the toxicant or isolated component substance of the sample may be elucidated according to standard laboratory techniques well known to those skilled in the art, such as mass spectroscopy (MS)[22]; high performance liquid chromatography (HPLC)[10,11,12,28]; infrared spectroscopy (IR)[23]; nuclear magnetic resonance (NMR)[22,24]; thin layer chromatography (TLC)[9,26]; x-ray crystallography[22,23] and the like.

As used in the present application, the term "luminescent" biological agent is defined as an organism or an extract of an organism, which emits heatless light under appropriate conditions. Most luminescent systems involve the use of molecular oxygen. Luciferin (a pigment) and a specialized form of a luciferase enzyme are included in many luminous organisms and enables these organisms to emit a heatless light in the presence of oxygen. Cypridina is an example of a marine organism which contains the luciferin pigment. For example, Cypridina contains a luciferin which, when reacted with the Cypridina luciferase enzyme in the presence of oxygen, emits a heatless bioluminesence. *Vibrio fischeri*[16] and *Vibrio harveyi*[17] contain an enzyme necessary to make light, a well as two reagent compounds (a long-chained aliphatic aldehydes and a vitamin derivative, which is a yellow pigment flavin mononucleotide. In reduced form (i.e., in the presence of oxygen) the pigment glows and allows the organism to emit a heatless light. For example, Cypridina contains a luciferin which, when reacted with the Cypridina luciferase enzyme in the presence of oxygen, emits a heatless bioluminescence. Similarly, fire flies possess a luciferin pigment which in the presence of the firefly luciferase and oxygen, provides a bioluminescence suitable for use in the practice of the present invention. *Photobacterium leiognathia* is a bacteria which is strongly bioluminescent. All organisms and plants which possess a luciferin/luciferase system would be included among those luminescent biological agents which could be used in the practice of the claimed invention.

The present invention also provides a kit for the identification of a toxicant in a sample, which includes a luminescent biological (for example, bacterial) agent. In a particularly preferred embodiment, the kit comprises a carrier means adapted to receive at least two container means and at least one separation phase matrix in close confinement therewith; at least one separation phase matrix; a first container means comprising a luminescent biological agent; and a second container means comprising a diluent for the luminescent biological agent.

Most preferably, the luminescent biological agent is a luminescent bacteria, such as *Vibrio fischeri* (ATCC No. 7744), *Photobacterium phosphoreum, Photobacterium leiognathi*, or *Vibrio harveyi* (ATCC No. 33843). In a most preferred embodiment of the kit, the luminescent biological agent is in a lyophilized form. Where the luminescent biological agent is in a lyophilized or dried form, the kit will include a diluent suitable for reconstituting the particular biological agent into its "glowing" form.

By way of example, where the luminescent biological agent is a luminescent bacterial agent, and the particular luminescent bacterial agent is a marine bacteria, a suitable diluent would comprise a salt solution of at least 1% by weight NaCl. A saline solution between 1% to 4% NaCl is even more particularly preferred. Most preferably, the diluent should constitute 3% by weight NaCl.

The diluent of the kit most preferably is a buffering agent which includes an NaCl concentration of the diluent should be a concentration which maximizes the luminescent characteristics of the particular marine bacterial species employed. The salt concentration of the diluent has been observed by the Inventors to affect the intensity of the bacteria's luminescence, and thus the bacteria's suitability as a "visualizing" agent for the described method. For example, where the luminescent bacteria is *Vibrio fischeri*, a marine luminescent bacteria, the diluent is most preferably about 0.5 M NaCl. Other diluents for marine luminescent bacteria may comprise a saline solution between 0.6–0.66 M NaCl (1%–4% by weight NaCl).

The separation phase matrix may comprise a chromatography paper sheet, a TLC plate, a Sepharose matrix, or virtually any matrix which is capable of separating a mixed sample into discernable, at least partially isolated, components. The separation phase matrix most preferred for use in the described kit is a TLC plate.

Most preferably, where the method to be used to isolate the components of the sample is paper chromatography, the chromatography paper sheet is most preferably Whatman chromatography paper 1M or 3M. Where the method for separation is TLC, the most preferred TLC plates are Whatman adsorption plates flexible backed aluminum or polyester #4410-222 plates.

The luminescent bacterial agent is to be suspended in a saline solution diluen. Where the bacteria is stored in lyophilized form, the lyophilized bacterial agent is reconstituted in the referenced saline diluent to regain its luminescent form prior to use.

Attempts by the Inventors of directly laying a TLC plate on the luminescent bacteria provided relatively low-sensitivity (i.e., a large amount of inhibitor substance or toxicant needed to be present to demarcate the presence of any isolated substance) for detection, as the discernable "zones" of luminescent inhibition were relatively faint. Therefore, most preferably, the reconstituted bacterial agent is placed into an aspirator spray bottle and sprayed onto sample-exposed separation phase matrix, (for example, the sample-exposed chromatography paper sheet or TLC plate).

The method of directly spraying a TLC plate with a suspension of the luminescent bacteria was demonstrated to provide the best results, with clearly defined "zones of luminescent inhibition" and wherein even minor (less distinct) zones of luminescent inhibition are discernable. At this time, spray application of the luminescent biological reagent thus constitutes the best mode for practicing this aspect of the invention.

However, other methods for achieving contact of the luminescent biological agent to a test sample may be employed to identify substances and/or toxicants in a sample. For example, a sheet of film with an agarose or acrylamide layer, or other solid surface or gel containing a rehydratable material therein capable of being stored in sheet form and rehydratable prior to use, are contemplated by the Inventors as constituting equally usable methods for practicing the claimed invention.

In such an embodiment, a dehydrated form of the luminescent biological agent would be incorporated into a porous or water permeable material which was amenable to being formed into a sheet form. The sheet, so impregnated with a dehydrated form of the luminescent biological agent, would be stored in dry form until needed for use. For use, the sheet with the bacterial agent in it should be rehydrated in a suitable rehydrating agent, such deionized water or a saline solution. Where the luminescent biological agent is a marine luminescent bacteria, such as *Vibrio fischeri*, the rehydrating agent would most preferably be a saline solution of at least 1% NaCl. Most preferably, the saline solution should be between 1–4% NaCl. A 3% NaCl solution is most preferred.

After the sheet has been rehydrated, the now "glowing" sheet would be laid over a sample of isolated component substances/toxicants to render the luminescent biological agent in contact with the test sample component substances. The existance of zones of luminescent inhibition could then be examined to identify potential toxicants of the sample.

The claimed invention also comprises a luminescent bacterial agent which is capable of identifying in isolatable form a component or mixture of components, substances or a toxicant in a sample. The presence of isolatable component substances or toxicants in a sample is visualized through the presence of discernable zones of inhibition surrounding the applied luminescent bacterial reagent (i.e., termed "zones of luminescent inhibition").

Any luminescent bacteria may be employed in the practice of the present invention. However, those luminescent bacterial agents preferred in the practice of the invention include *Photobacterium phosphoreum, Photobacterium leiognathi, Vibrio fischeri*, (ATCC Acc. 7744) and *Vibrio harveyi* (ATCC Acc. 33843). Among these exemplary bacteria, the *Vibrio fischeri* and *Vibrio harveyi* bacteria embody the even most preferred luminescent bacterial agents of the invention. The *Vibrio fischeri* (ATCC Acc. No. 7744) constitute the most particularly preferred embodiment of the claimed luminescent bacterial agent of the present invention.

As a method for identifying component substances in a sample, using a luminescent biological agent, the claimed method comprises: preparing a luminescent biological agent; obtaining a sufficient volume of the sample to provide a test sample; separating the component substances of the test sample by applying the test sample to a separation phase matrix to provide isolated component substances; and exposing the isolated component substances to a volume of the luminescent biological agent in a concentration sufficient to identify the isolated component substances of the sample. One or more zones of luminescent inhibition will become apparent on the luminescent biological agent-exposed separation phase matrix, and thus identify the isolated component substances in the sample. The concentration of luminescent biological agent sufficient to identify the isolated component substances of a sample is referred to as a "substance indicating amount". Where the test sample is being analyzed to identify potential toxicant(s), the amount of luminescent biological agent is defined as "toxin indicating amount". The necessary concentrations to provide this "indicating" effect is between $10^8$–$10^9$ bacterial cells/ml of diluent where the bacterial agent is contacted with the sample in the form of a liquid suspension.

Where paper chromatography is the technique used to separate component substances or toxicants in a test sample, chromatography paper (as the separation phase matrix) and an appropriate solvent system are used. Corresponding segments on a separate chromatogram (sample plus chromatography sheet) not exposed to luminescent bacteria may be used to obtain additional volumes of the component substances/toxicants of the sample, or where desired, to further chemically identify the isolated component substances of the sample. Additional sample or chemical analysis of the sample in purer form may be accomplished for example, by cutting out the chromatography paper segments (not exposed to luminescent bacteria) which correspond to the identified "zones of luminescent inhibition"; and eluting the isolated substances from the cut out chromatography paper segments with an appropriate solvent.

The isolated component substances or potential toxicants of the sample may then be analyzed using standard chemical and spectral means to chemically identify the isolated substances of the sample. If necessary, the eluate of the isolated components of the sample may be concentrated by techniques well known to those skilled in the art prior to chemical and spectral analysis to chemically identify the isolated substance or toxicant of the sample.

The luminescent biological agent of the claimed method may comprise a luminescent bacteria, a luminescent fungi, a luminescent fish extract, a luminescent dinoflagellate, a luminescent firefly extract, luminescent anthrogans, luminescent earthworm extract, luminecent coelenterate extract or a luminescent crustacean. (Cypridina organisms).

Most preferably, the luminescent biological agent is a luminescent bacteria, such as *Vibrio fischeri* (ATCC acc. 7744) *Vibrio harveyi* (ATCC Acc. 33843), *Photobacterium phosphoreum*, or *Photobacterium leiognathi*. The term "luminescent biological agent" as used in the present application may include an organism which has been modified to possess luminescence such as an organism genetically engineered to include the luciferase gene. According to the claimed methods, the test sample may comprise a liquid sample, a solid sample, or a gaseous sample. Most preferably, the sample is to be prepared as a liquid test sample for separation via a TLC plate separation phase matrix.

While the present methods may be used to isolate and identify virtually any substance(s) or toxicant(s) in a sample which is capable of inhibiting the luminescence of a luminescent biological agent (for example, a luminescent bacterial agent), preferred applications of the present method include the identification of isolated substances such as pesticides, herbicides, heavy metals and their salts, and plant extracts, from a sample. By way of example, pesticides which may be identified according to the present methods include DIAZANON®, LINDANE® and SEVIN®. By way of example, herbicides which may be identified according to the present methods include ROUNDUP® and WEED-B-GON®. Heavy metals which may potentially be identified according to the present methods include the identification of mercury, lead, cadmium and their respective salts.

According to the present method, the isolated substance or toxicant(s) in the sample may be chemically analyzed by any combination of laboratory techniques well known to those of skill in the art for the chemical characterization of an isolated or partially isolated substance. For example, MS, IR, NMR, HPLC, thin layer chromatography, etc are standard techniques which may be used to further chemically define an isolated substance in a sample. Any of these common laboratory techniques may be used alone or in combination to identify the chemical structure of substantially purified component substances or potential toxicants in a sample.

According to one preferred embodiment of the present method, wherein the separation technique is paper chromatography (separation phase matrix is chromatography paper), the developed chromatogram (having thereupon any isolatable component substances or toxicants of the sample) may be exposed to the luminescent bacterial agent by spraying a suspension of the luminescent bacterial agent, most preferably suspended in a saline solution, onto the developed chromatogram.

As the agent used to visualize the components/toxicants of a sample is of a biological nature, and therefore potentially sensitive (i.e., inhibited by chemicals) to components of a desired solvent to be used, failure to remove solvent could in itself cause nonspecific inhibition of luminescence. Thus, application of the luminescent bacterial suspension should be done after the complete evaporation of carrier solvent from the chromatogram. In addition, the developed chromatogram should also be allowed to dry a second time, after the separation solvent has passed through the sample "streaked" or "spotted" chromatogram, before the luminescent biological (for example, luminescent bacterial agent) is applied (for example sprayed) to the chromatogram.

Observation of a chromatogram exposed to the luminescent agent (the "sprayed" chromatogram) should be made while the chromatogram is still wet or at least moist with the suspension of luminescent biological reagent applied thereto. For example, luminescent bacteria are very sensitive to dehydration, and thus luminescence would be lost everywhere if the investigator does not examine the chromatogram within at least 1 hour of exposing the bacteria to the chromatogram. In practice, a bacteria-sprayed chromatogram remains moist and glowing from the luminescent biological agent for as long as 45 minutes to one hour, depending on the humidity of the environment.

The Inventors herein demonstrate that the inhibition of luminescence of particular species of luminescent bacteria employed according to the methods described herein, is discriminating as among potential toxicants and/or isolated component substances of a test sample. For example, the Inventors have found that the luminescence of one particular species of luminescent bacteria, *Vibrio fischeri*, is not inhibited by the pesticide, VOLCK oil spray. Neither does the luminescence of the *Vibrio fischeri* appear to be immediately inhibited by calcium ion. Moreover, all of the luminescent inhibition effects demonstrated through the use of luminescent bacteria, particularly *Vibrio fischeri*, are concentration dependent.

The methods of the present invention may be adapted for use in the identification of closely related components which may be present together in a test sample. For example, selective sensitivities as between different luminescent biological agents, particularly as between luminescent bacteria, may be used to tailor the disclosed method for use in a particular industry, or to test specific product lines. For example, the luminescence of the bacterial agent *Vibrio fischeri* is more sensitive to the pesticide DIAZANON® than to the pesticide LINDANE®. Similarly, the luminescence of this particular bacterial agent is more sensitive to the inhibitory action of SEVIN® as compared to LINDANE®. Selection of *Vibrio fischeri* bacteria would thus be indicated as particularly suitable for use in the described method where a sample is suspected to contain pesticides, such as in a pesticide production facility, or perhaps where foodstuffs are stored.

Thus, the particular species of luminescent bacteria may be selected on the basis of the specific use for which it is intended (i.e., for the identification of a particular class of related substances). For example, where an Investigator wishes to isolate and identify particular pesticides, he/she may select a luminescent bacteria which demonstrates a particular sensitivity to pesticides in general, over another, perhaps less sensitive, luminescent bacteria, for the analysis of a sample which may likely include pesticides. Therefore, a hierarchy of relative toxicant sensitivity, in regard to both the class of toxicant and particular luminescent bacteria, can be established.

The present invention provides a rapid (about 35 minutes) technique that can potentially identify a wide variety of environmentally and biologically harmful substances.

The Inventors have found that the methods described herein are capable of identifying herbicides and pesticides at their working strengths (i.e., DIAZANON®, LINDANE®, ROUNDUP® AND WEED-B-GON® diluted 1/150). Therefore, herbicides, pesticides and other environmental pollutants and contaminants may be identified according to the present method with the described kits as they occur in the environment in the air, in lakes, streams, ground water and in run-off from fields, for example, in relatively dilute form (for example diluted 1/1,000 from commercial stock concentration).

As used in the present disclosure, the term "toxicant" and "identified isolated component substance" of a sample is defined as a substance which is capable of inhibiting the luminescence of a luminescent biological agent, such as a luminescent bacteria, *Vibrio fischeri*.

Even more specifically, the term "toxicant" is broadly defined as a substance which is capable of inhibiting or potentially lethal to, a virus or a living organism, such as a plant, animal or microorganism. Even more specifically a toxicant potentially toxic to an animal such as a human may be identified using the described method. Toxicity to bacteria is recognized as an indication of toxicity of a substance to higher organisms, including humans. The Inventors hypothesize that forms of the biological agents which are represented by whole organisms, rather than extracts of whole organisms, will be both more sensitive and also be capable of identifying a broader range of substances and toxicants in a sample in smaller concentrations than with luminescent extracts from an organism.

As used in the present application, the term bioluminescence more specifically refers a living organism or from extracts of a living organism when combined under appropriate conditions. Lack of luminescence refers to the lack of light emission not necessarily related to the expiration of the organism.

The following abbreviations are used throughout the Specification:

| | | |
|---|---|---|
| ECD | = | Electron Capture Detection |
| TLC | = | Thin Layer Chromatography |
| NMR | = | Nuclear Magnetic Resonance Spectroscopy |
| M | = | Molar |
| HPLC | = | High Performance Liquid Chromatography |
| IR | = | Infra-Red Spectroscopy |
| MS | = | Mass Spectroscopy |
| D | = | Dimension |
| THF | = | Tetrahydrofuran |
| UV | = | Ultraviolet |

DETAILED DESCRIPTION OF THE PREFERRED EMBODIMENTS

Figure 1:
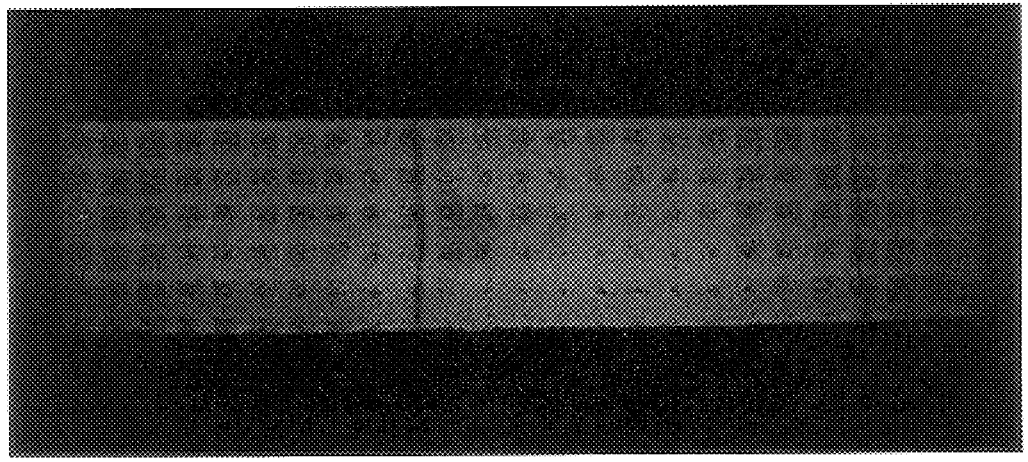
FIG. 1—TLC plate with garlic extract sample in $H_2O$. Not exposed to luminescent bacteria. TLC Plate identified those components which are ultraviolet light-absorbing. If compound absorbs the 254 nM light, then area where compound is located will not glow, and appears as a dark spot (V shape) in a garlic extract using fluorescent detection (254 nM excitation). Solvent used is 80:8:12 mixture of ($H_3CCN:H_2O:NH_3$). The V-shaped areas are not indicative of a bacteriotoxic agent. Results from these analysis indicate a compatible system for resolving ultraviolet absorbing and thereby identifiable components in a sample.

The present invention provides methods, kits and luminescent biological (for example, bacterial) agents which are demonstrated to be surprisingly advantageous for the identification of specific toxicants or component substances in a sample. Moreover, techniques are proposed wherein the identified component substances of a sample may subsequently be chemically characterized or additional volumes of the isolated component ingredient (i.e., toxicant) be obtained employing a variety of chemical techniques in conjunction with the teachings of the present disclosure.

The novel use of a luminescent biological agent together with a separation phase matrix provides a unique method for the rapid and simple identification of potentially toxic (isolated) substances in a sample. The Inventors foresee the application of the present invention in the laboratory as well as in industry for the detection of environmental pollutants, particularly in water resources. Additionally, use of the described methods in the development and identification of therapeutically valuable components in plants and organisms, such as in garlic, is also considered an important application of the described invention.

Luminescent Bacteria as the Luminescent Biological Agent

Where the luminescent biological agent to be used is a luminescent bacterial agent, such as the luminescent bacteria *Vibrio fischeri*, the bacteria should constitute a suspension of bacteria at a final concentration of about $10^8$–$10^9$ bacteria cells/ml in the suspension to be used, for example, where the luminescent bacterial agent is sprayed onto a chromatogram.

A preferred method whereby the luminescent bacteria are prepared for use in the presently described invention is as follows. The bacteria must first be allowed to become fully "induced" in their luminescent system, i.e., the luminescent system of the bacteria should be allowed to reach complete development prior to harvesting of the bacteria from the culture. Determination of at what point a bacteria has reached full luminescent system development is well known to those of skill in the art[30,31].

Upon full development of the luminescent system of the bacteria, the bacteria should be harvested and then placed in a centrifuge tube. The bacteria are then to be centrifuged at a speed of 10,000×G for 30 minutes at room temperature. Thus centrifuged, the bacteria will form a pellet of cell "paste" at the bottom of the tube. About 1 gram of this cell paste (about 12 ml of cell "paste"=1 gram) of glowing bacteria is then to be diluted to a volume of 20 ml, by adding 20 ml of a diluent of choice. Where the luminescent bacteria is a marine bacteria, for example, the diluent is most preferably a buffered saline solution of between 1–4% NaCl. As diluted to 20 ml, the cell suspension constitutes a concentration of $10^{10}$–$10^{12}$ bacteria cells/20 ml (or $10^8$–$10^9$ cells/ml).

The following Examples are presented only to describe preferred embodiments and utilities of the present invention, and to satisfy best mode requirements. The examples are not meant to limit the scope of the present invention unless specifically indicated otherwise in the claims appended hereto. The following Examples are provided to demonstrate various aspects of the present invention.

Example 1—Isolation of Identifiable Luminescent Inhibitory Toxicant In Garlic Extract Using Luminescent Bacteria.
Prophetic Example 2—Proposed Chemical Identification of Toxicants in a Garlic Extract.
Example 3—Identification of Pesticides in Sample With Luminescent Bacteria.
Example 4—Dilution Series of DIAZANON® or TLC with *Vibrio fischeri*.
Example 5—Solvent Polarity and Fluorescent and Bioluminescent Detection of DIAZANON®.
Example 6—Identification of Pesticides and Herbicides in a Sample with Luminescent Bacteria.
Example 7—Identification of Herbicides and Pesticides.
Prophetic Example 8—Proposed Identification of Heavy Metals In a Sample with Luminescent Bacteria.
Prophetic Example 9—Proposed Chemical Identification of a Toxicant In a Sample Isolated With Bioluminescence Methods.
Example 10—Identification of Toxicant in a Gaseous Phase Sample with Luminescent Bacteria.
Prophetic Example 11—Proposed Identification of a Toxicant on a Solid Surface Sample with Luminescent Bacteria.
Prophetic Example 12—Proposed Test Kits for Identifying Toxicants in a Sample.

EXAMPLE 1

Isolation of Identifiable Luminescent Inhibitory Toxicant In Garlic Extract Using Luminescent Bacteria The present example is presented to describe a method by which components of a substance which inhibit luminescent bacteria may be isolated. The sample analyzed in the present example is a garlic extract. For this experiment, the Inventors first prepared a garlic extract from garlic powder. The garlic powder was processed so as to form a liquid garlic extract. One (1) gram of garlic powder was blended with 5 ml. $H_2O$. Other solvents such as ethanol, chloroform, or acetone may be used to blend the sample, but $H_2O$ was found to be the best solvent for the garlic.

A 5 ml. volume of the garlic extract was first applied ("spotted") to TLC plates at several points equidistant from one edge of the plate. The plate was inverted in a sealed TLC solvent container with a small amount of solvent in the bottom such that spotted samples were parallel to and above the solvent interface.

Figure 2:
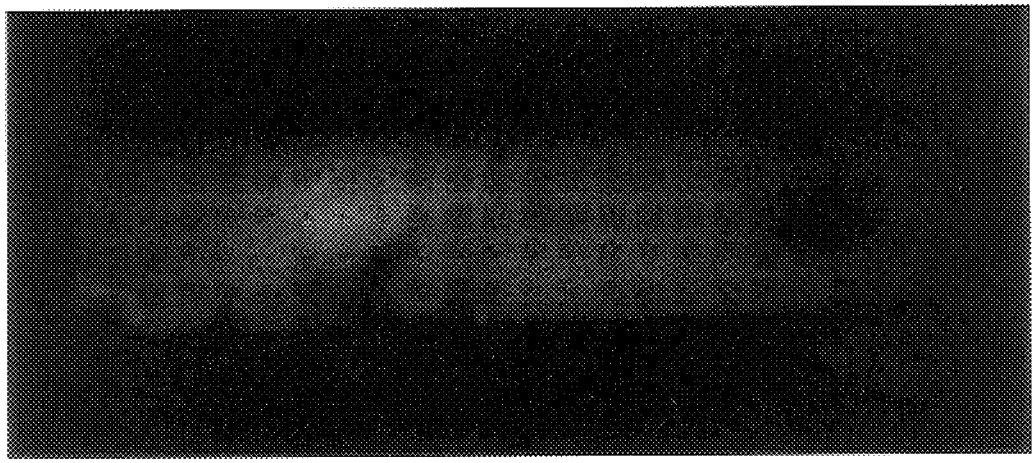
FIG. 2—TLC plate with garlic extract sample exposed to luminescent bacteria, *Vibrio fisheri*, same solvent as FIG. 1. Bioluminescence inhibition is evident as a dark circular region (about 10.5 cm from bottom of plate). This circular region is hypothesized to constitute allicin in the garlic extract.

As the solvent (acetonitrile:water:aqueous ammonia, 8:1.5:0.5) migrated up the TLC plate, the individual components in the garlic extract were sufficiently separated to detect separate zones of luminescent inhibition upon exposing the developed chromatogram to a suspension of luminescent bacteria, *Vibrio fischeri* applied in a suspension of 0.5 M NaCl (See FIGS. 1–2).

The Inventors applied the luminescent bacteria, *Vibrio fischeri* to the chromatogram specifically by spraying the described suspension of bacteria (contained in a buffered salt solution of 3% (0.5 M) NaCl at a pH of about 7) onto the developed chromatogram after the solvent in which the sample was contained had evaporated. Zones of luminescent inhibition were located prior to the dehydration of the bacteria on the chromatogram, i.e., at least within 1 hour after application of the bacteria.

The inhibition of bioluminescence of the bacteria caused by the presence of toxicants in isolated components of the garlic extract was then visualized. The bioluminescent inhibition effect of any toxicant in the garlic extract became apparent generally within a few minutes in the form of a clearly demarcated zone of bioluminescent inhibition (See FIG. 2). These zones of bioluminescent inhibition are areas on the chromatogram which were dimmer (i.e., less brightly emissive) than the more brightly emissive surrounding areas on the chromatogram (which did not include isolated components of the garlic extract which were capable of inhibiting the luminescence of the *Vibrio fischeri*). The areas wherein the chromatogram demonstrated greatest amounts and intensity of blue bioluminescence from the applied *Vibrio fischeri* bacteria identified areas of no component substances or instead isolated components of the garlic extract which were not toxic to the bioluminescence of the bacteria, and therefore according to the described method were considered not to constitute toxicants.

As stated, the inhibition of bacterial luminescence which occurs when a toxicant is detected, becomes apparent very soon, often within a few minutes, and grows more distinct with time and reaching a pronounced peak effect in the minutes before the chromatogram dries out, i.e., the zones of decreased luminescence show more contrast relative to the surrounding luminescence with time, prior to the chromatogram drying out. When the chromatogram is dried out, of course, all the luminescence of the bacteria on the chromatogram will be extinguished with the dehydration of the bacteria.

Curiously, with the described methods, those positions on the chromatogram to which the toxicants have migrated (i.e., the "zones of inhibition") appear to dry out faster than the remainder of the chromatogram which, for example, remains highly luminescent.

Alternatively, the identification of the different individual components of the garlic extract could have been accomplished using paper chromatography as the separation phase matrix for the sample or other such techniques well known to those of skill in the art.

FIG. 1—TLC Plate of Garlic Extract

This is a photograph of a TLC plate viewed by fluorescence. The actual plate was 20 cm by about 4.5 cm. In the photograph the plate is seen reduced to 13.0 cm by 2.95 cm. Dimensions below refer to dimensions of the photograph not of the original plate.

Sample: Aqueous Garlic Extract. Preparation: 1.0 g of powdered garlic suspended in 5.0 ml of $H_2O$. Mixed with Vortex mixer for 1 minute. Centrifuged in table top centrifuge on high (about 1–2000 rpm, 60 seconds) to obtain straw yellow supernatant: the sample. Five $\mu l$ applied at origin of plate: pencil lines seen near 1.7 cm from bottom of plate. The application zone is seen as a circle (faint) of about a 6 mm diameter centered on the line.

Development: The solvent system used was acetonitrile: water: 25% ammonia (aqueous); 80:8:12. The sample was chromatographed in a closed chamber for approximately 20 minutes. The solvent front traveled about ⅘ of the distance of the plate. A faint demarkation line is seen at about 10.5 cm from the bottom of the plate showing the location of this solvent front.

Results: Major features of the chromatogram viewed by fluorescence excitation are a pronounced dark line at about 7.9 cm from the bottom of the plate several chevron or V-shaped dark areas in the 5.8–7.7 cm from the bottom region and a faint roughly circular shaped zone centered at about 8.8 cm from the bottom. The chevron shaped darkenings represent chemical components in the garlic resolved by the chromatographic process. The more or less circular zone at 8.8 cm (which can be more dramatically revealed by moving the photograph back and forth about 2 cm in the plane of the photograph) is the zone or near the zone of bioluminescence inhibition seen in photograph 2.

FIG. 2—TLC Plate of Garlic Extract

This is a photograph of a TLC plate (not the same one as in photograph 1, but a plate developed in an identical fashion except for a longer time) viewed by the emission of *Vibrio fischeri* luminous bacteria. The actual plate was 20 cm by about 4.2 cm. In the photograph the plate dimensions are 12.9 cm by 2.8 cm.

Sample: Aqueous garlic extract: the identical sample used in chromatogram of photo 1.

Development: same as in photo 1 except chromatogram ran longer, front reaching near the end of plate, near 12.5 cm in photograph. The origin was centered on the pencil line visible at about 2.4 to 2.5 cm from bottom of plate.

Results: A very dark, nearly circular zone is seen centered at about 10.5 cm from bottom of plate. A faint second zone is seen at about 6.7 cm from the bottom. Several darkened regions can be seen at the edges of the plate. The dark areas which appear at the edges are artifacts, and represent places on the chromatogram sheet which were not adequately sprayed with the luminous bacterial suspension. The zone at 10.5 cm represents the lumotox effect i.e., the determination of the location of the component in garlic which inhibits the luminous bacteria.

Routinely, for preliminary analysis of the chromatograms, the plates were irradiated with a lamp emitting UV (254 nm) radiation. The TLC plate used had the $F_{254}$ backing and were therefore fluorescent everywhere that no UV absorbing samples or components existed. This preliminary detection system also revealed component substances as dark spots on a light background where heterocyclic or other UV absorbing compounds were present. However, fluorescent extinction and luminescence inhibition were often not in parallel. For example, some samples presented as very dark zones, as viewed by fluorescence (for example, garlic), had little or no bioluminescence inhibition, while other zones presented very faint or non-existent fluorescence extinction but had substantial ability to inhibit (extinguish) bioluminescence (e.g., garlic, LINDANE®, ROUNDUP®).

Particular sources of TLC plates and chromatography sheets include Sargent Welch (No. S18953-10-TLC plate with $F_{254}$ fluorescent material), Analtech (uniplate taperplate silica gel G-F, No. 81013), and Eastman-Kodak (Kodak chromatogram sheets silica gel absorbent with fluorescent indicator, catalog no. 122-4294) and Whatman (absorbent plates flexible-backed aluminum polyester, catalog no. 4410-22 (contains fluorescent indicator)).

The Albert et al. article[22] provides a description of analyzing mevinolin, a fungal metabolite employing standard laboratory techniques such as mass spectroscopy, nuclear magnetic resonance and x-ray analysis. These alternative standard laboratory techniques could be utilized to analyze eluted components from an unknown sample.

Upon isolation/separation of the various components in the garlic extract sample by a chromatography method, the inventors then applied the luminescent bacteria to the developed chromatogram. Most preferably, the luminescent bacteria is applied to the developed chromatogram in the form of a suspension contained in a buffered salt solution (about 0.3 M $Na^+/K^+$ phosphate buffered saline (3% NaCl by weight) pH 7.0).

PROPHETIC EXAMPLE 2

Proposed Chemical Identification of Toxicants In a Garlic Extract

The present prophetic example is provided to outline one proposed method by which the toxicant(s), as identified according to the method of the procedure outlined in Example 1 may be further characterized to identify the chemical structure of the isolated toxicant(s). This method may also be used where additional amounts of the isolated substance are desired or where the purity of the isolated substance is to be determined.

The particular "zones of luminescent inhibition" described above, which provide for the isolation of the component substances (i.e., toxicant) in the test sample, are used as reference points to isolate each component substance from an adjacent spotted sample which was run on the same or a separate TLC plate with the same sample. Unsprayed sections of the TLC plate, which correspond to zones of luminescent inhibition on the sprayed portion, may be scraped off and added to a sufficient volume of an appropriate solvent (i.e., distilled water, acetone, ethanol, ether, ethyl acetate-chloroform or other solvent mixtures) such that the isolated component substance of the sample may become dissolved in the solvent.

Subsequent removal of the solid TLC scrapings from the liquid eluate can be accomplished by various methods known in the art such as centrifugation or filtration. If necessary, the eluates containing dissolved toxicants may then be concentrated using standard techniques. These separated, (and in some cases, concentrated) isolated substances of the sample may be further resolved in other TLC solvent systems (or HPLC, paper chromatography, and the like) to verify purity or to obtain suitably pure isolated substances. These substantially pure isolated substances can then be identified using standard chemical and spectral methodologies. For example, such standard chemical and spectral methodologies include as HPLC, MS, IR, NMR, and the like.

Alternatively, two dimensional (2D) thin layer (TLC) can be run for higher resolution of the sample for more explicit identification of components therein. In the 2D method, a sample is spotted near one corner of the TLC sheet or plate, and run successively in two, usually perpendicular, directions, using different solvent systems or conditions. For example, the sample is chromatographed in the usual way (described above) on the TLC medium in the first direction using solvent system No. 1 (e.g., a basic non-polar system, ammonia:butanol:hexane in a 5:20:75 ratio). The chromatogram, containing components resolved in a linear fashion in this solvent system No. 1, is then to be removed from the chromatography chamber, dried fully to remove solvent molecules of this system No. 1 solvent, and then the thus dried chromatogram is rotated 90° to the orientation first used and chromatographed in the new orientation using a solvent system No. 2 (e.g., a polar, acetic system, such as acetic acid, acetone, ethanol in a 10:50:40 ratio). The components resolved into a linear array by system No. 1 move in the perpendicular direction with the solvent system 2 to provide even greater resolution of individual component substances in the sample.

This same basic approach can be utilized where luminescent bacteria are used to identify isolated component substances of a sample separated by paper chromatography systems, either 1D or 2D. As those in the art will appreciate, in using such systems, there are various ways to achieve separation such that toxicants can be obtained in relatively pure form. For example, another version of 2D paper chromatography may employ electrophoresis in one dimension and gravitational flow paper chromatography or isoelectric focussing in another dimension, or other two-dimension combination thereof (i.e., 1st D=paper chromatography, 2sn D=isoelectric focusing, etc.)

EXAMPLE 3

Identification of Pesticides in Sample With Luminescent Bacteria

The present example is provided to demonstrate the use of the claimed methods and reagents for the identification of a pesticide in a sample of known substances. In this example, the pesticides identified were DIAZANON®, LINDANE® and SEVIN®. The luminescent bacteria used in the present example was *Vibrio fischeri* (ATCC 7744).

Figure 6:
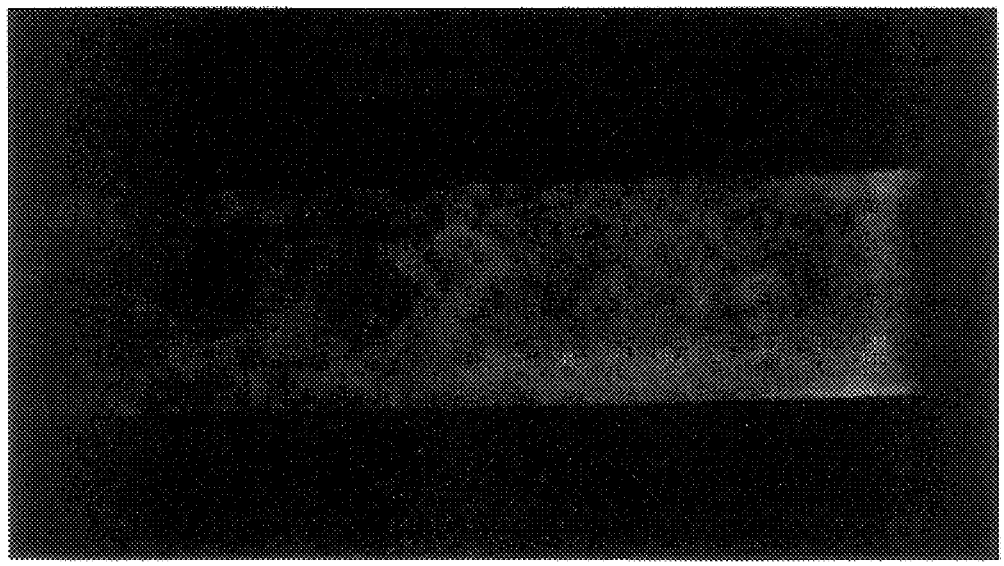
FIG. 6—TLC for DIAZANON® dilution series with the luminescent bacteria, *Vibrio fischeri* (same dilutions as for FIG. 5).

Identification of these individual pesticides and herbicides was achieved essentially according to the same methods described in Example 1. A suspension of *Vibrio fischeri* in a saline diluent was sprayed, using an aspirator bottle, on the developed chromatograms. Zones of luminescent inhibition appeared surrounding those areas on the plate where the DIAZANON® had migrated. Similar, less dim zones of inhibition, where LINDANE® had migrated (See FIGS. 6 and 7). In a similarly run TLC with SEVIN®, the chromatogram also demonstrated zones of luminescent inhibition at those areas on the chromatogram where SEVIN® had migrated.

Figure 3:
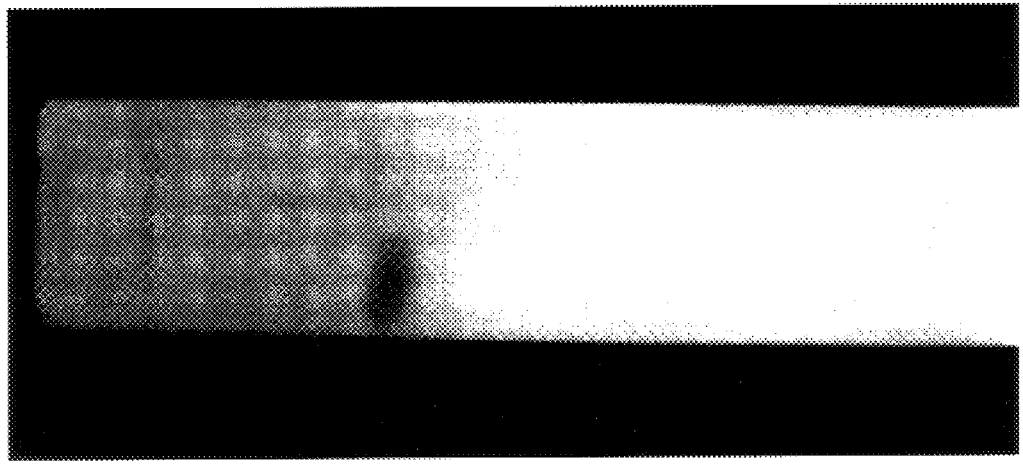
FIG. 3—TLC plate with DIAZANON® and LINDANE® by fluorescence.
Figure 4:
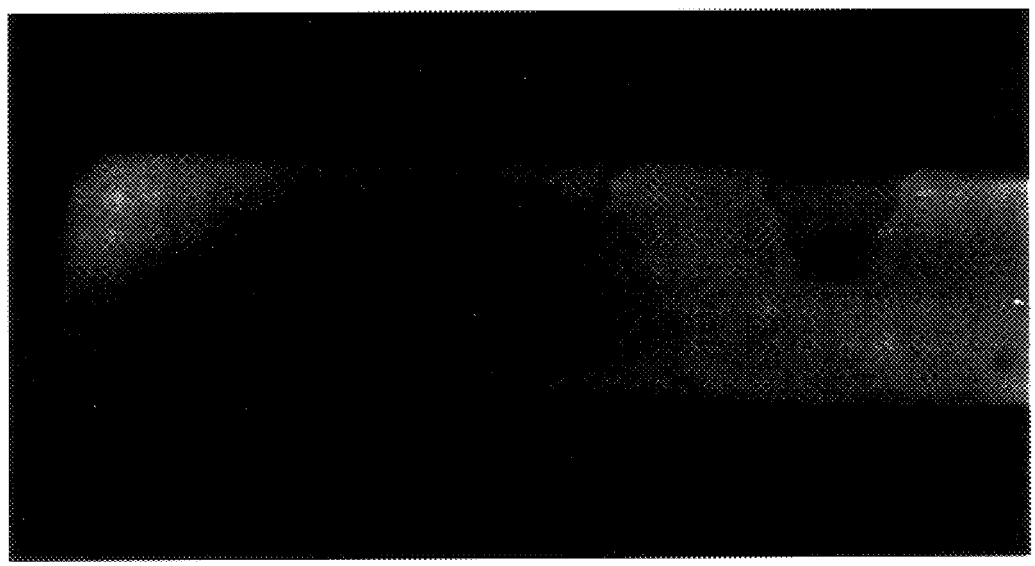
FIG. 4—TLC plate DIAZANON® and LINDANE® by bioluminescence.
Figure 5:
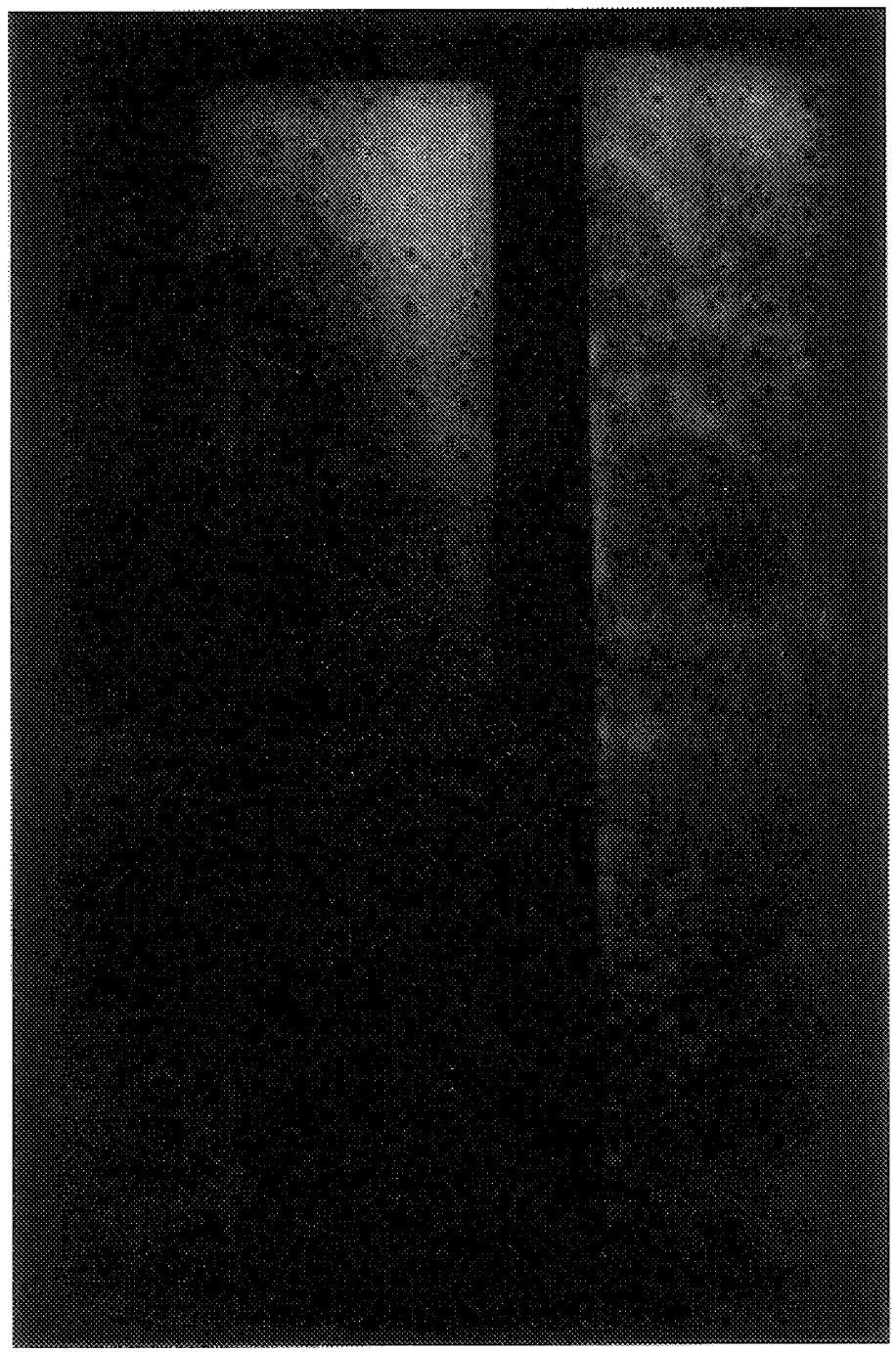
FIG. 5—TLC for DIAZANON® dilution series. Plates demonstrate a dilution series of DIAZANON®. The presence of DIAZANON® is demonstrated at dim areas defining the "zone of luminescent inhibition" of the luminescent bacteria, *Vibrio fischeri*, in response to the pesticide. Dilutions employed of the pesticides were full strength, 1:128; 1:256; 1:512 and 1:1024.

FIGS. 3 and 4

These are photographs of the same TLC plate taken by two different conditions: Fluorescence and Bioluminescence, respectively.

Samples: 5 µl samples of (1/32 by DIAZANON®) and (1/8 LINDANE®). The DIAZANON® sample was produced by serial dilution of the commercial diagram (25% w/v) 0,0, diethyl-0-[2-isopropyl-6-methyl-⋞-pyrimidinyl] phosphorsthionate, Ortho Products. The DIAZANON® was diluted with ethanol by factors of 2 until a dilution of 1/32 commercial strength was reached. The LINDANE® (Ortho Products) was diluted in ethanol from the commercial 20% (w/v) gamma isomer of benzene hexachloride, until a final strength of 1/8 was reached.

Development: Acetonitrile: 25% Aqueous ammonia, 75:25

Results: FIG. 3 represents the results from this study using DIAZANON® and LINDANE® on a TLC plate viewed by 254 nm excitation. A prominent dark zone for DIAZANON® is located at 8.8 cm from bottom of FIG. 3. About 3 quite faint zones for LINDANE® at 8.2, 9.2, and 10.3 cm from bottom of FIG. 3 are demonstrated. DIAZANON® origin (application spot) at 2.5 cm from bottom of photo, LINDANE® origin at 3.0 cm.

FIG. 4 viewed by bioluminescence from *vibrio fischeri*. Dark zone for DIAZANON® very close to zone for fluorescence extinction (at about 8.1 cm from photobottom). Several very dark zones for LINDANE® at about 8.0, 8.8, and 10.0 from photobottom. Also seen is slight inhibition zone at origin of LINDANE® sample. The several zones for LINDANE® indicate that several isomers or different inhibition compounds are present in the LINDANE® sample.

EXAMPLE 4

Dilution Series of DIAZANON® on TLC with *Vibrio fischeri*

The present example is provided to demonstrate the sensitivity of the claimed invention to detect relatively low concentrations of a pesticide. An exemplary pesticide for demonstrating the sensitivity of the assay used here is DIAZANON®.

FIGS. 5 AND 6

Spot tests of DIAZANON® at several dilutions were performed at the following strengths: full strength (25% w/v DIAZANON®), 1:128; 1:256; 1:512; and 1:1024. No chromatography was done. 5 µl samples of the various DIAZANON® dilutions were applied to TLC plate material, sprayed with a suspension of *Vibrio fischeri* in a saline solution (3% NaCl WT/VOL.) and photographed. Marked inhibition occurred up to and including the D/256 dilution (D/252 appears by clerical mistake on sheet instead of D/256 which was used) of full strength (25% w/v) DIAZANON®. Faint inhibition is seen at dilution 1:512 and dilution 1:1024 (See FIG. 6, R).

The TLC plates with DIAZANON® demonstrate that the methods described herein are sufficiently sensitive to identify a pesticide in a sample at concentrations in which they are likely to occur in a land or water sample obtained in the environment.

EXAMPLE 5

Solvent Polarity and Fluorescent and Bioluminescent Detection of DIAZANON®

The present example is presented to demonstrate the effect of varying the solvent polarity on the detection patterns, or "zones of inhibition" of *Vibrio fischeri* in the presence of DIAZANON®, a pesticide.

Figure 7:
FIG. 7—TLC of DIAZANON® with either UV 254 fluorescence or bioluminescence inhibition with luminous bacteria, *Vibrio fischeri* in a sample.
Figure 8:
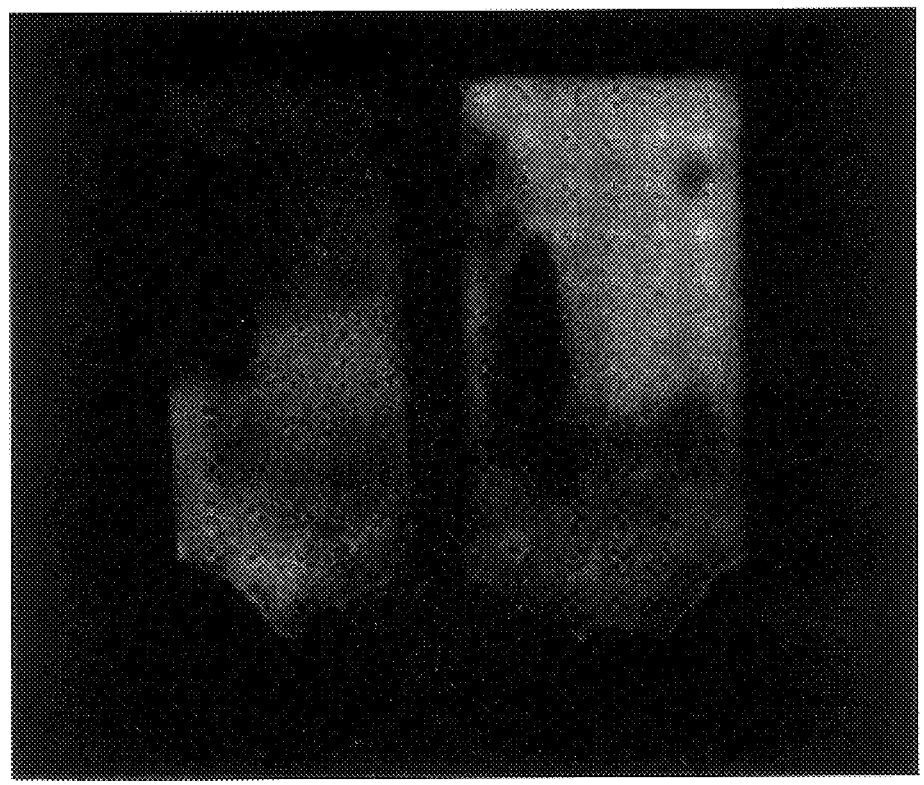
FIG. 8—TLC of DIAZANON®, ROUNDUP® and WEED-B-GON® identified at a dilution of 1/150 (working strength). Luminescent bacteria exposure time prior to examining the bacteria-sprayed plates was 35 minutes.

FIGS. 7 and 8 provide photographs of TLC plates viewed by 254 nm irradiation (FIG. 7) and by bioluminescence (FIG. 8).

Samples: In each case, 5 µl of (DIAZANON®/8) was applied at origin on left and 5 µl of LINDANE®/8 was applied at right origin.

Development: Three solvent systems used. All composed of Hexane:THF mixtures. In FIG. 7 the left chromatogram was Hex:THF, 70:30 the middle chromatogram was Hex:THF, 80:20 the right chromatogram was Hex:THF, 90:10.

(middle chromatogram contains clerical labeling error of 80 THF:20 HEX, which should be 80 HEX:20THF)

Results: FIG. 7 shows the decrease in polarity as the proportion of THFs lowered causes the DIAZANON® and faint LINDANE® spots or zones to be progressively diminished in mobility; to have smaller $R_f$ values; to migrate shorter distances from the origin.

Figure 9:
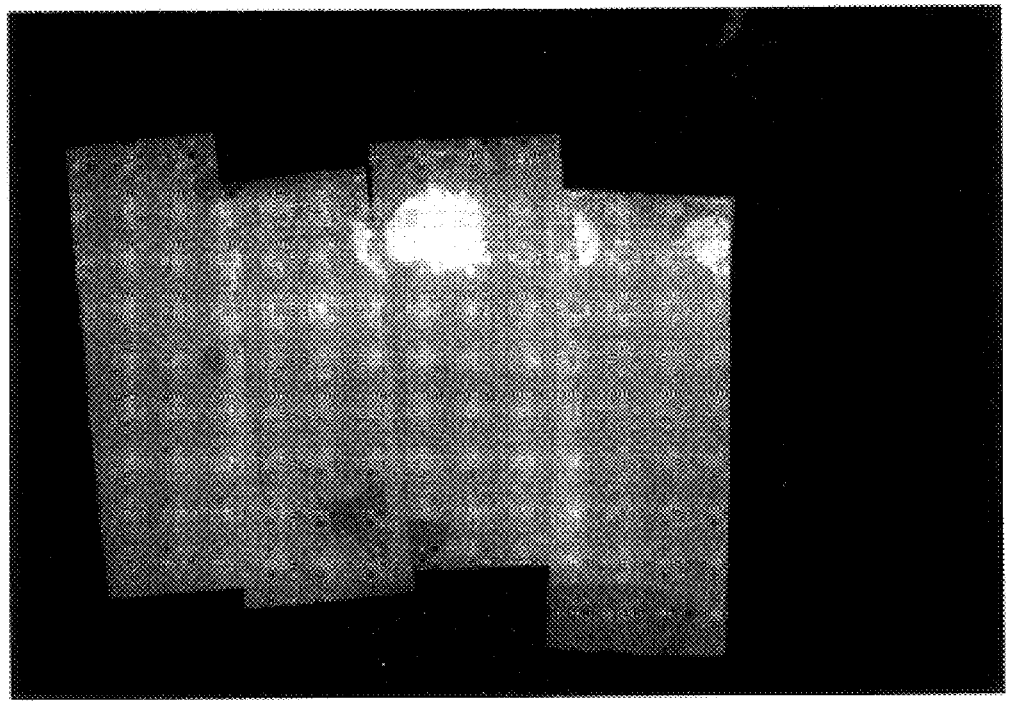
FIG. 9—TLC plates of two pesticides, DIAZANON® and LINDANE® and two herbicides, ROUNDUP® and WEED-B-GON®, taken in room lighting. Dilution of pesticides and herbicides=1/150.

FIG. 8 shows only the left-hand and right-hand TLC plates seen in FIG. 9. Dark bioluminescence zones of inhibition are seen in Photo 8 for DIAZANON® and LINDANE® samples.

EXAMPLE 6

Identification of Pesticides and Herbicides in a Sample With Luminescent Bacteria The present example is provided to demonstrate the use of the claimed methods and reagents for the identification of pesticides and herbicides in a known test sample using a luminescent biological agent.

In this example, the herbicides ROUNDUP® and WEED-B-GON® and the pesticides DIAZANON® and LINDANE® are identified in a test sample with the luminescent bacteria, *Vibrio fischeri* (ATCC 7744).

EXAMPLE 7

Identification of Herbicides and Pesticides

Each sample was run on an individual TLC sheet. Photographs of the resulting 4 individual chromatograms are presented at FIG. 9 (room light) and FIG. 10 (Bioluminescence—chromatogram with luminescent bacteria).

Two solvent systems were used. The solvent systems used to identify the herbicides (ROUNDUP® and WEED-B-GONE®) was 100% ethanol. A 5 ml sample of an 8-fold dilution of these commercially available herbicides was used in the spotting of the TLC plates.

The solvent system used for the pesticides DIAZANON® and LINDANE® was Hexane:THF, 90:10. The pesticides were spotted at a concentration of 1.8. A 5 ml sample of an 8-fold dilution of these commercially available pesticides was used in the spotting of the TLC plates.

Two solvent systems were employed as no single system has yet been found to adequately resolve all compounds (i.e., the two pesticides and the two herbicides). Use of 100% ethanol causes DIAZANON® and LINDANE® to run at the front of the solvent system. Use of 90% Hexane, 10% THF causes ROUNDUP® and WEED-B-GONE® to stay at the origin. The TLC plates photographed are in the following order (left to right) (one sample per plate): DIAZANON®, LINDANE®, ROUNDUP®, and WEED-B-GONE®. In each case, the commercial strength was diluted by a factor of 8.

Results:
a. Pesticides

Figure 10:
FIG. 10—TLC plates of two pesticides, DIAZANON® and LINDANE® and two herbicides, ROUNDUP® and WEED-B-GONE® viewed by bioluminescence showing zones of luminescent inhibition.

The DIAZANON® sheet did present an entirely distinct "zone of inhibition", but the FIG. 10 only marginally indicates this characteristic, perhaps due to partial bacteria dehydration. The LINDANE® chromatogram presented as a distinct zone of inhibition culminating in a dark spot center about 2.9 cm from the bottom of the plate.

The ROUNDUP® chromatogram presented a clear zone of inhibition as seen at the origin, and at least one other inhibition zone centered at 4.5 cm from the bottom of the plate. The WEED-B-GONE® chromatogram presented as a large oval zone of luminescent inhibition (perhaps comprised of several components) starting at about 1.8 cm from the bottom of the TLC plate and stretching to beyond 6 cm from the bottom of the plate.

EXAMPLE 7

Identification of Herbicides and Pesticides

The following example presents the results of three separately run experiments by the Inventors. These data demonstrate the reliability of the described methods for consistently identifying a component substance in a sample. The following list represents a description of the particular herbicides and pesticides, and the percent dilutions used thereof, in the described 3 separately run TLC plates.

WEED-B-GON®
  10.8% w/v dimethylamino salt of 2,4 dichlorophenoxyacetic acid 11.6% w/v dimethylamino salt of 2-(2-methyl-4 chlorophenoxy)propionic acid DIAZANON®
  25% w/v O,O,diethyl-O-[2-isopropyl-6-methyl-4-pyrmidinyl]phosphorothio(n)ate ROUNDUP®
  41% w/v isopropylamino salt of glycophosphate N-(phosphoromethyl)glycine LINDANE® (bark and leaf mineral spray)
  20% w/v gamma isomer of benzene hexachloride liquid LIQUID SEVIN® CARBAMYL
  27% w/v 1-naphthyl-N-methyl carbamate The following table presents the results obtained for identifying DIAZANON®, LINDANE®, ROUNDUP®, and WEED-B-GON® in three different tests conducted by the Inventors. These data demonstrate that the described method provides a system which possesses the ability to detect, with varying sensitivity, a variety of herbicides or pesticides in a sample on a consistent and reliable basis, as demonstrated by the closely corresponding "spots" for each run of the same component substance between the three separately run chromatograms.

TABLE 1

| Herbicide/Pesticide | Distance of Front | Spot 1 | Spot 2 | Spot 3 | Ratio of Front Fluor | Ratio of Front Biolu | Stan. Dev. |
|---|---|---|---|---|---|---|---|
| Test 1 | | | | | | | |
| DIAZANON ® | 2.38 | 0.63 | — | — | 0.26 | 0.26 | 0.02 |
| LINDANE ® | 2.38 | .88 | 1.38 | 1.66 | 0.37 | 0.37 | 0.02 |
| | | | | | 0.58 | 0.57 | 0.00 |
| | | | | | 0.70 | — | — |
| ROUNDUP ® | 2.36 | 0.00 | 0.13 | 1.38 | 0.00 | 0.00 | 0.00 |
| | | | | | 0.06 | — | — |
| | | | | | 0.58 | — | — |
| WEED-B-GON ® | 2.36 | 0.66 | 1.64 | 1.88 | 0.28 | 0.28 | 0.02 |
| | | | | | 0.69 | 0.69 | 0.04 |
| | | | | | 0.80 | — | — |
| Test 2 | | | | | | | |
| DIAZANON ® | 2.75 | 0.68 | — | — | 0.26 | 0.25 | 0.01 |
| LINDANE ® | 2.19 | 0.83 | 1.23 | 1.55 | 0.38 | 0.35 | 0.03 |
| | | | | | 0.56 | 0.57 | 0.00 |
| | | | | | 0.70 | — | — |
| ROUNDUP ® | 2.00 | 0.00 | 0.12 | 1.22 | 0.00 | 0.00 | 0.00 |
| | | | | | 0.06 | — | — |
| | | | | | 0.61 | — | — |
| WEED-B-GON ® | 2.25 | 0.65 | 1.35 | 1.79 | 0.28 | 0.28 | 0.020 |
| | | | | | 0.66 | 0.66 | .01 |
| | | | | | 0.80 | — | — |
| Test 3 | | | | | | | |
| DIAZANON ® | 2.79 | 0.68 | — | — | 0.24 | 0.24 | 0.00 |
| LINDANE ® | 2.09 | 0.83 | 1.23 | 1.59 | 0.39 | 0.40 | 0.01 |
| | | | | | 0.58 | 0.60 | 0.03 |
| | | | | | 0.73 | — | — |
| ROUNDUP ® | 2.13 | 0.00 | 0.21 | 1.29 | 0.00 | 0.00 | 0.00 |
| | | | | | 0.10 | — | — |
| | | | | | 0.60 | — | — |
| WEED-B-GON ® | 1.84 | 0.38 | 1.17 | 1.55 | 0.21 | 0.21 | 0.05 |
| | | | | | 0.64 | 0.63 | 0.02 |
| | | | | | 0.84 | — | — |

$R_f$ Values Represented in the Reported Values in the Table;
$R_f$ = relative to the front; a fractin of the total distance which the solvent front migrated.

PROPHETIC EXAMPLE 8

Proposed Identification of Heavy Metal Salts In a Sample With Luminescent Bacteria The present prophetic example is provided to present a use of the claimed methods and reagents for the identification of a heavy metal in a sample. Specifically, the Inventors hypothesize that the described methods would be useful in the identification of the heavy metals such as mercury, lead and cadmium using the described luminescent biological reagents, such as the bacteria, Vibrio fischeri (ATTC Acc. No. 7744).

In the present example, the Inventors spotted the various metals on to a chromatography paper sheet, but did not run them through a chromatography separation process. Upon spotting of the various metals along one side of a chromatography paper sheet, the sample spots were allowed to dry. Upon drying, the spotted sheets were exposed to the luminescent bacteria Vibrio fischeri. Employing this method, the Inventors were able to visualize the presence of the heavy metal salts of mercury, lead, and cadmium.

To isolate the heavy metal spotted on the chromatography paper, the paper edge at which the sample was spotted should be exposed to a solvent system, most preferably an acidic solvent system.

Specific reference is made here to the RAININ® catalog[29], wherein a standard technique (for the separation of heavy metals) is described using an ion chromatography metals column. Resolution of $Pb^{++}$ and $Cd^{++}$ is demonstrated in the reference RAININ® catalog.

Successive equal volumes of a heavy metal could be eluted using the HPLC procedure from the HPLC machine and spotted in an array or in a linear fashion on a sheet of (Whatman) chromatography paper. After the carrier solvent is evaporated or otherwise removed by drying, the sheet could be sprayed with a suspension of luminescent bacteria, such as Vibrio fischeri, as described. Zones of bioluminescent inhibition could be similarly visualized to identify the metal.

PROPHETIC EXAMPLE 9

Proposed Chemical Identification of a Toxicant In a Sample Isolated With Bioluminescence Methods The present prophetic example is provided to outline a proposed method whereby the identified region provided on a chromatography sheet with the described luminescent agent, particularly a luminescent bacteria may be analyzed to ascertain the chemical identity of an isolated component substance of a sample.

A volume of sample containing sufficient concentration of toxicants would be applied to a chromatography paper, such as Whatman 1M or 3M and chromatographed using a solvent system which provides maximum separation of the sample components. Various solvent systems may be utilized and tested for separation efficiency as well understood by those skilled in the art. Small amounts of sample may be used to test for improved resolution in one dimensional (1D) chromatography solvent systems. Those solvents found most effective may then be utilized for larger scale separation on large sheets of chromatography paper for two-dimensional chromatography (2D).

Two dimensional chromatography may be necessary to resolve sample ingredients for subsequent identification of substantially pure compounds. By determining a combination of two solvent systems which effectively resolve the component toxicants, 2D chromatography can be run in duplicate.

Following the chromatography, the luminescent bacteria may be sprayed onto one of two identical sample sheets. Areas on the sheet which demonstrate a decreased luminescence would then be used to mark the corresponding areas of the unsprayed sheet. The corresponding areas on the unsprayed sheet are cut out and eluted with distilled water, appropriate solvents such as acetone or ethanol or a solvent mixture to provide individual, substantially pure toxicants for identification. This procedure can be repeated, and/or multiple 2D sheets may be run simultaneously, in order to accumulate sufficient quantities of various substantially pure toxicants.

In this manner, appropriate amounts of toxicants in a sample may be separated and then identified using standard chemical procedures. For example, small amounts of the purified component substances may be run on high pressure liquid chromatography (HPLC) and compared to known standards for identification[15]. As will be appreciated by those skilled in the art, additional standard techniques used for chemical identification may be employed such as spectral analysis: Mass spectra, infrared spectra (IR), nuclear magnetic resonance (NMR), and the like.

It will understood by those skilled in the art that multiple 2D chromatography sheets can be run simultaneously in which different sheets are sprayed with different luminescent bacteria. This would provide a more thorough analysis of toxicants which may be detectable by one luminescent bacterium, but not by another. Additionally, combinations of different luminescent bacteria in one spray solution may facilitate the thorough identification of most or all of the detectable isolated component substances in a sample. In this manner, a thorough analysis and identification of toxicants in a sample may be undertaken.

Essentially this same approach can be taken using thin layer chromatography (TLC), instead of paper chromatography as described above, for the initial separation and identification of toxic substances in a sample. Multiple TLC plates (e.g., Whatman 4856-840 with 1,000 $\mu$M silica layer) may be run simultaneously in the same solvent system-utilizing 1D or 2D runs, as described above, for paper chromatography. In such a TLC approach to toxicant identification, toxicants would be identified by spaying the plates with luminescent bacteria, marking the zones of decreased luminescence, and scraping off the corresponding areas on the unsprayed portions of plates. The scrapings are then eluted with an appropriate solvent, such as distilled water, acetone or ethanol or a solvent mixture, concentrated (if required), and identified using HPLC, MS, IR, NMR, and the like.

By following either of the above procedures, the separation and identification of toxicants in a sample can be accomplished simply and rapidly. The standardization of this method to be used for the identification of toxicants in certain types of samples will be appreciated by those skilled in the art as providing simple, rapid, and inexpensive methodologies for toxicant identification. For example, certain types of samples (i.e., industrial effluent) could be tested to determine the initial separation system, the solvent systems, the luminescent bacteria (or combinations of luminescent bacteria), the elution protocol, and any subsequent techniques for quantitation and/or identification.

Through the use of standard curves of easily quantitated known compounds, the percent recovery in a given separation system can be determined. In this manner, amounts of identified toxicants can be quantitated and extrapolated back to the original sample volume applied. For example, the use of radiolabeled compounds, of known specific activity, which are separated by paper or TL chromatography, eluted, and counted for radioactivity, would provide an indication of the percentage recovery of a given compound. By comparing various radiolabeled chemical compounds in a given identification system (paper or TLC with different solvents and the like), one could correct for recovery losses of a given identification system.

When the separated toxicants are quantitated by certain chemical and spectral methods, the quantities may then be extrapolated to determine the quantities of individual toxicants present in the original sample. Thus, this method, in many cases, would allow for toxicant quantification.

These steps could be standardized into kits tailored for the analysis of specific types of samples (i.e., a kit for a certain industrial effluent or certain biological samples, such as foodstuffs, pharmaceuticals, and the like). These kits would comprise certain solvents and luminescent bacteria which would effectively resolve specific sample types thereby greatly simplifying and reducing the cost of toxicant detection, identification, and quantitation.

Alternatively, an unknown sample may be processed by the above procedure for identification and quantitation.

PROPHETIC EXAMPLE 10

Identification of Toxicant in a Gaseous Phase Sample With Luminescent Bacteria The present prophetic example is provided to outline a proposed method whereby an investigator may identify a toxicant present in a gaseous phase sample employing the methods with luminescent bacteria described herein.

As an initial step, the gaseous sample would be collected by techniques known to those skilled in the art. For example, a gas sample might be collected by filtration through a solid filter such that toxicants deposit onto the filter or by aspiration into a liquid such that toxicants dissolve in the liquid. In the case of a solid filter, the filter could then be eluted with distilled water or a suitable solvent, concentrated, chromatographed by paper or thin layer chromatography, and identified using certain luminescent bacteria as described in Example 6.

PROPHETIC EXAMPLE 11

Identification of a Toxicant on a Solid Surface Sample With Luminescent Bacteria The present prophetic example is provided to outline a proposed method whereby a toxicant on a solid surface sample may be identified with the described luminescent bacteria.

As in Example 7, methods for removing a toxicant from a solid surface so that it is collected in a concentrated liquid form will vary depending on the nature of the solid surface. Techniques for such removal will be apparent to those skilled in the art. Using the procedures outlined in Example 6, one skilled in the art would be capable of identifying and quantifying toxicants which were eluted from or removed from the solid surface. Alternatively, for direct detection of toxicants, the solid surface could be sprayed with a certain luminescent bacteria, or mixture of more than one luminescent bacteria, such as *Vibrio fischeri* and the surface observed for zones of decreased luminescence (i.e., zones of luminescent inhibition) substantially as has already been outlined in Example 1. Of course, these isolated component substances of the sample (potential toxicants) could then be chemically analyzed according to laboratory techniques well known to those of skill in the art to identify the chemical structure of the isolated component. By way of example, such laboratory techniques for determining the chemical structure of an isolated component substance include HPLC, MS, IR, NMR, and the like.

PROPHETIC EXAMPLE 12

Proposed Test Kits for Identifying Toxicants in a Sample

The present prophetic example is provided to define those components which would comprise a proposed test kit useful for the identification of toxicants in a sample. Such a kit most preferably would comprise a carrier means adapted to receive at least two container means and at least one chromatography paper sheet in close confinement therewith. The kit should also include at least one chromatography paper sheet and a first container means comprising a luminescent bacterial agent. While any luminescent bacterial agent may be used in conjunction with the described kit, that bacterial agent most preferred is the *Vibrio fischeri* (ATTC Acc. No. 7744). Most preferably, the luminescent bacterial agent should be in lyophilized form in the container means. The lyophilized bacteria would then be suspended in a diluent solution. For example, where appropriate NaCl concentrations are within the lyophilized sample, deionized water may be employed as the diluent solution without any expected deleterious effects to the luminescence of the bacteria.

In a second container means, the kit should further comprise a diluent for a luminescent bacterial agent. Most preferably, the diluent should comprise a 0.5 M NaCl buffered saline solution at pH 7 where the bacteria is a marine bacteria and has not been lyophilized to include NaCl. The kit may optionally also include a separation solvent, such as acetonitrile, deionized water, or aqueous ammonia.

In other proposed forms of the presently proposed kit, the kit may further comprise an aspirator spray bottle to facilitate the easy application of suspended luminescent bacteria to a separation phase matrix such as a TLC plate or chromatography paper, chromatogram. In addition, the kit may comprise several vials of lyophilized luminescent bacteria. In other proposed forms of the presently proposed kits, the kit may further comprise instructions for the suspension and application of the luminescent bacteria to facilitate visualization of the isolated component substances of the test sample, and also in regard to the reaction time to be allowed and at what point the luminescent bacteria-exposed separation phase matrix should be read.

BIBLIOGRAPHY

The following references are specifically incorporated herein by reference in pertinent part.
1. Drucker et al. (1984) E.P. 153366.
2. Vasseur et al. (1983), presented at the International Symposium on Ecotoxicological Testing for Marine Environment, Belgium, pp. 12–14.
3. Baher (1988)—WPI 88-308491 (884).
4. Liebowitz (1984), *Anal. Biochem.*, 137(1):161–163.
5. Gu, Z. (1987), *Turangxue Jinzhan* 15 (3):48–51).
6. Siemens (1990)—WO 88 DE 626—; WPI ACC No. 90-116654(9016)—Genlux Fursch. Biol. Verfahren.
7. Strom et al. (1986), *ACTA Hydro Chim Hydrobiol.*, 14 (3):283–292.
8. Ugarova et al. (1987), *Appl. Biochem. Biotechnical.*, 15(1):35–51.
9. *Thin Layer Chromatography: A Laboratory Handbook* 2nd ed, E. Stahl, Ed., Springer-Varlag, New York, N.Y., (1967).
10. *HPLC of Small Molecules: A Practical Approach* C. K. Lim; Ed., IRL Press, Oxford England (1986).
11. *HPLC of Macromolecules: A Practical Approach* R. W. A. Oliver, Ed., IRL Press, Oxford, England (1989).
12. *Plant Drug Analysis: A Thin-Layer Chromatography Atlas*, H. Wagner, S. Bladt, E. M. Zgainski, Springer-Verlag (eds.), New York, N. Y. (1984).
13. Alltech Bulletin, (1991) #183, *Gas Chromatography Apparatus*, p.11.
14. Thompson, B. C., Kugmack, J. M., Law, D. w., Winslow, J. J., eds. (1989), "Copolymeric Solid Phase Extraction for Quantitating drugs of Abuse in Urine by Wide-Bore Capillary Gas Chromatography" L C-G-C 7(10):846–850.
15. Merck Index, 11th ed. (1989), p. 878–879.
16. Johnson, F. H., (1972) *J. Bact.*, 109:1101–1105.
17. Hastings, J. W., MAV (1973) *Arch. Mikrobiol.*, 94:283–330.
18. Yetison, T., (1978) *Appl. Environ. Microbio.*, 36:11–17
19. Williamson, K. L., (1989), *Macroscale and Microscale Organic Experiments*, D.C. Heath and Company, Lexington, Mass. ISBN 0-669-19429-8.
20. Shriner, R., Fuson, R., Curtin, D., *The Systematic Identification of Organic Compounds*, John Wiley and Sons, Inc., New York, Fifth Edition, (1964).
22. Alberts et al. (1980) *Proc. Natl. Acad. Sci., U.S.A.*, 77(7):3957–3961.
23. Pannell et al. (1990) *Organometallics*, 9(9):2454–2462.
24. Hertel et al. (1991) *J. Am. Chem. Soc.*, 113:657–665.
25. Fischer Scientific Catalog (1991–1992), p. 483.
26 Kamminga, D., (1985), *J. Chromatog.* 330:375–378.
27. Günther, K., (1988) *J. Chromatog.*, 448:11–30.
28. Armstrong, D. W., 91984) *J. Liquid Chromatography*, 7:353–376.
29. Rainin Scientific Catalog (1991–1992), p. 3–38.
30. *Bioluminescence and Chemiluminescence: Basic Chemistry and Analytical Applications*, Marlene A. DeLuca and William D. McElroy, eds., Academic Press (1981)
31. *Bioluminescence and Chemiluminescence*, In: *Methods in Enzymology*, Marlene A. DeLuca, eds., Academic Press, Vol. 57 (1978).
32. G. W. Mitchell and J. W. Hastings (1971) *Analytical Biochemistry* 39:243.
33. J. W. Hastings and G. Weber (1963), *J. Opt. Soc. Am.*, 53:1410.

What is claimed is:

1. A method for identifying the presence of a toxic substance in a sample using a luminescent biological agent, said method comprising the steps of:
   (a) preparing a luminescent biological agent suitable for use in conjunction with a separation phase matrix;
   (b) obtaining a test sample suspected to contain a toxic substance;
   (c) separating said toxic substance from other substances present in said test sample by applying said test sample to said separation phase matrix; and
   (d) exposing said separated toxic substance to a luminescent biological agent to identify the presence of said toxic substance by detecting inhibition of luminescence.

2. The method of claim 1, wherein the luminescent biological agent is selected from the group consisting of a luminescent bacteria, a luminescent fungi, a luminescent fish extract, a luminescent dinoflagellate, a luminescent firefly extract, a luminescent anthozoan, a luminescent earthworm extract, a luminescent coelenterate extract and a luminescent crustacean.

3. The method of claim 1, wherein the luminescent biological agent is a luminescent bacteria or extract thereof.

4. The method of claim 3, wherein the luminescent bacteria is selected from the group consisting of *Photobacterium leiognathi, Photobacterium phosphoreum, Vibrio fischeri*(ATCC Acc. No. 7744) or *Vibrio harveyi*(ATCC Acc. No. 33843).

5. The method of claim 1, wherein the luminescent biological agent is *Vibrio fischeri*(ATCC Acc. No. 7744) or *Vibrio harveyi*(ATCC Acc. No. 33843).

6. The method of claim 1, wherein the luminescent biological agent is *Vibrio fischeri*(ATCC Acc. No. 7744).

7. The method of claim 1, wherein the test sample is a liquid sample, a solid sample or a gaseous sample.

8. The method of claim 1, wherein the separation phase matrix is high performance liquid chromatography (HPLC) and the test sample is a liquid sample.

9. The method of claim 8, wherein the separated toxic substance is eluted from the HPLC and spotted in an array or in a linear fashion on a sheet of chromatography paper.

10. The method of claim 9, wherein the presence of said toxic substance is detected by spraying the sheet of chromatography paper with a volume of luminescent bacteria to detect inhibition of luminescence.

11. The method of claim 10, wherein a volume of the luminescent bacteria comprises a suspension of $10^8$–$10^9$ bacterial cells/ml.

12. The method of claim 1, wherein said toxic substance comprises a substance selected from a pesticide, herbicide and heavy metal.

13. The method of claim 12, wherein said pesticide is selected from O,O,diethyl-O-(2-isopropyl-6-methyl-4-pyrimidinyl) phosphorothionate, gamma isomer of benzene hexachloride liquid and 1-naphthyl-N-methyl carbamate.

14. The method of claim 12, wherein said herbicide is selected from isopropylamino salt of glycophosphate-n-(phosphoromethyl) glycine or a mixture of dimethylamino salt of 2,4 dichlorophenoxyacetic acid and dimethylamino salt of 2-(2-methyl-4 chlorophenoxy) propionic acid.

15. The method of claim 12, wherein said heavy metal is selected from mercury, lead and cadmium, or salt thereof.

16. The method of claim 1, wherein said toxic substance comprises a plant extract, with the proviso that said plant is not garlic.

17. The method of claim 1, wherein said toxic substance is toxic to a virus.

18. The method of claim 1, wherein said toxic substance is toxic to a plant.

19. The method of claim 1, wherein said toxic substance is toxic to an animal.

20. The method of claim 19, wherein said animal is a human.

21. A method for identifying the presence of a toxic substance in a sample using a luminescent biological agent, said method comprising:

(a) preparing a luminescent biological agent suitable for use in conjunction with a separation phase matrix;

(b) obtaining a test sample suspected to contain a toxic substance;

(c) separating said toxic substance from other substances present in said test sample by applying said test sample to said separation phase matrix; and (d) exposing said separated toxic substance to a luminescent biological agent to identify the presence of said toxic substances by detecting inhibition of luminescence, with the proviso that said toxic substance is not garlic.

22. The method of claim 1, wherein said toxic substance is one or more toxic substances.

* * * * *